(12) United States Patent
Maciejewski

(10) Patent No.: US 8,678,216 B2
(45) Date of Patent: Mar. 25, 2014

(54) HOUSING UNIT AND A MEDICAL IMAGING DEVICE COMPRISING A HOUSING UNIT

(75) Inventor: Bernd Maciejewski, Markt Erlbach (DE)

(73) Assignee: Siemens Aktiengesellschaft, Munich (DE)

( * ) Notice: Subject to any disclaimer, the term of this patent is extended or adjusted under 35 U.S.C. 154(b) by 149 days.

(21) Appl. No.: 13/230,178

(22) Filed: Sep. 12, 2011

(65) Prior Publication Data

US 2013/0066187 A1   Mar. 14, 2013

(51) Int. Cl.
*H01R 13/502*   (2006.01)
*H05K 5/00*   (2006.01)

(52) U.S. Cl.
CPC ............ *H05K 5/0004* (2013.01); *H01R 13/502* (2013.01)
USPC ......................................... 220/4.02; 174/561

(58) Field of Classification Search
CPC ... H05K 5/0013; H05K 5/0004; H01R 13/502
USPC ........ 220/4.02, 3.94, 3.92, 3.9, 3.7, 4.01, 3.2; 174/561, 560, 559, 542, 535, 520
IPC ....................................................... H01R 13/502
See application file for complete search history.

(56) References Cited

U.S. PATENT DOCUMENTS

| 1,471,340 | A | * | 10/1923 | Knight | 220/3.94 |
| 1,522,926 | A | * | 1/1925 | Wadsworth | 361/672 |
| 2,620,081 | A | * | 12/1952 | Lear, Jr. | 220/3.8 |
| 2,782,954 | A | * | 2/1957 | Antonucci | 220/3.92 |
| 3,168,613 | A | * | 2/1965 | Palmer | 174/50 |
| 3,214,126 | A | * | 10/1965 | Roos | 248/318 |
| 3,284,151 | A | * | 11/1966 | Herbert et al. | 312/244 |
| 3,376,086 | A | * | 4/1968 | Fisher | 312/100 |
| 3,877,601 | A | * | 4/1975 | Evans et al. | 220/3.3 |
| 4,151,926 | A | * | 5/1979 | Kinney et al. | 220/3.94 |
| 5,783,775 | A | * | 7/1998 | Marusinec | 174/50 |
| 2012/0326575 | A1 | * | 12/2012 | Hirota | 312/7.2 |

* cited by examiner

*Primary Examiner* — Robert J Hicks

(57) ABSTRACT

A housing unit for medical imaging devices is proposed. The housing unit has at least two housing shell units and a support frame unit for the purpose of mounting the at least two housing shell units. The at least two housing shell units in each case has at least one overlapping element. An overlap between the at least two housing shell units can be achieved in a region of the overlapping elements when the at least two housing shell units are in an assembled position on the support frame unit.

19 Claims, 4 Drawing Sheets

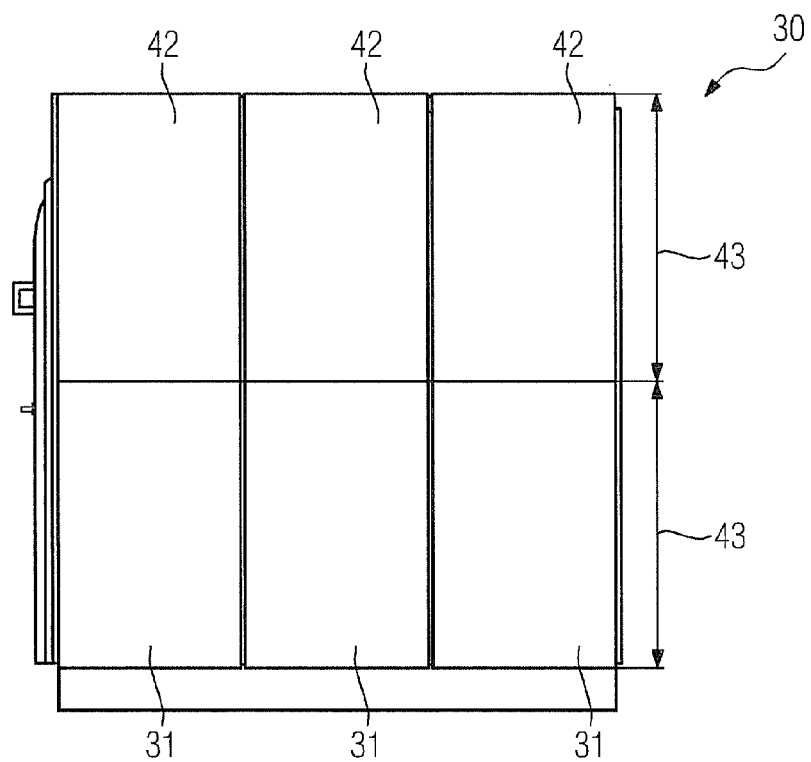
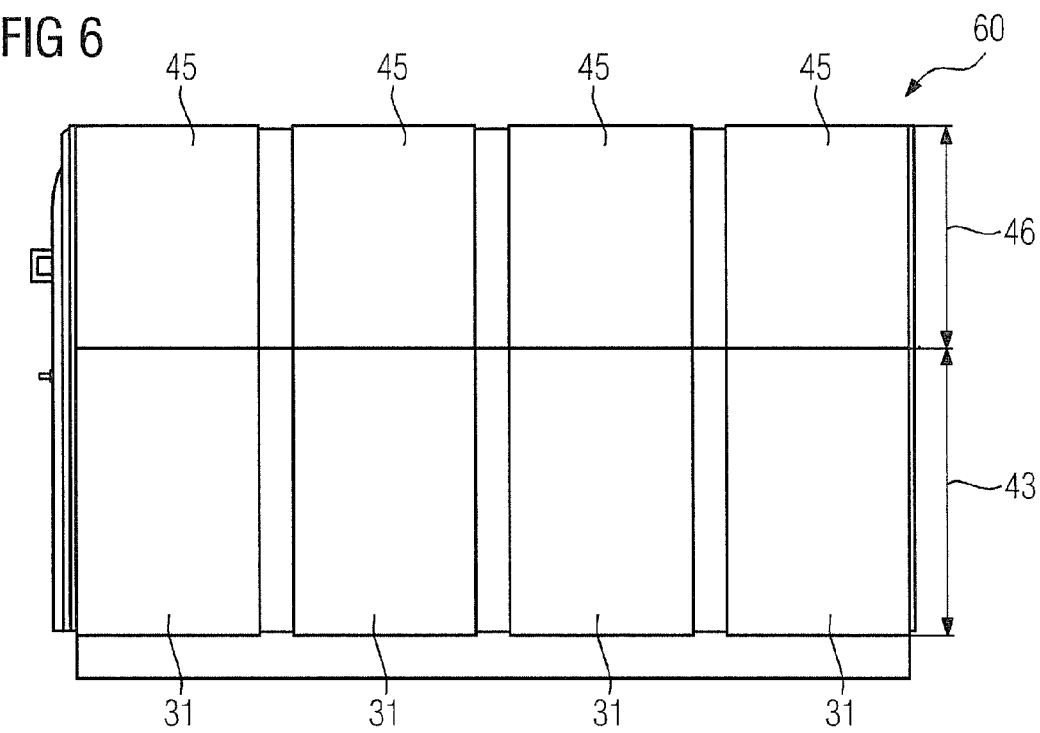

HOUSING UNIT AND A MEDICAL IMAGING DEVICE COMPRISING A HOUSING UNIT

FIELD OF THE INVENTION

The present invention relates to a housing unit, in particular for medical imaging devices, comprising at least two housing shell units and a support frame unit for mounting the at least two housing shell units.

BACKGROUND OF THE INVENTION

Medical imaging devices have different dimensions depending on the embodiment of a detector unit that is included in the medical imaging device and/or depending on the field of application, and therefore differently embodied housing units are used for the different medical imaging devices.

For example, depending on the field of application, differently embodied magnets are used for individual magnetic resonance devices. The differently embodied magnets differ, for example, in respect of a magnetic field strength and/or in respect of a use, e.g. as a whole body scanner or as a head scanner, etc. The differently embodied magnets also affect a geometric dimension of the individual magnetic resonance devices, which therefore require a housing unit that has been adapted to the magnetic resonance device in each case and includes an adapted housing cover. In this context, the individual housing units or housing covers for the different magnetic resonance devices differ in particular in respect of a length and/or a height and/or a width.

SUMMARY OF THE INVENTION

In particular, the present invention addresses the problem of providing an economical housing unit which can be used for differently embodied units and/or devices. The problem is solved by the features in the independent claims. Advantageous embodiments are described in the dependent claims.

The invention takes as its starting point a housing unit, in particular for medical imaging devices, comprising at least two housing shell units and a support frame unit which is used for mounting the at least two housing shell units.

It is proposed that the at least two housing shell units should have at least one overlapping element in each case, wherein by means of the overlapping elements a variable overlap between the two housing shell units can be achieved in a region of the overlapping elements when the at least two housing shell units are in an assembled position on the support frame unit. It is therefore possible in a structurally simple manner during an assembly process to adapt the housing unit to a dimension, e.g. a length and/or a height and/or a width, of a unit which is surrounded by the housing unit, e.g. a magnetic unit of a magnetic resonance device, by virtue of a variable overlap region that is available due to the overlapping elements. Moreover, the housing unit can be used in a particularly cost-effective manner for a multiplicity of different units, e.g. different magnetic resonance devices, because the housing unit can be adapted to a dimension of the unit, in particular a magnetic unit of the magnetic resonance device, by means of the overlapping elements. The overlapping element of a first housing shell unit and the overlapping element of a second housing shell unit are preferably arranged at opposite end regions of two adjacent housing shell units, such that a structurally simple arrangement of the housing shell units relative to each other can be achieved for differently embodied units. In this context, an overlapping element is understood in particular to mean an element of a housing shell unit, said element being specially designed to effect an overlap and/or superimposition relative to a further housing shell unit, in particular a further overlapping element of a further housing shell unit, wherein an overlap and/or superimposition can occur between two overlapping elements or between at least one overlapping element and a front cover of a magnetic resonance device, for example. For this purpose, the overlapping elements preferably have a smaller thickness than that of the remaining housing shell unit.

It is further proposed that the at least two housing shell units should comprise in each case two overlapping elements, which are arranged at opposite end regions of the housing shell units. It is thereby possible to achieve a large adjustment region for the purpose of adapting the housing unit to a dimension of the unit that is surrounded by the housing unit, e.g. a magnetic unit, due to a plurality of overlap regions and/or superimposition regions, one overlap region and/or superimposition region being arranged between two housing shell units in each case. As a result of the significant flexibility of the housing unit with respect to a height and/or a length and/or a width of a unit, e.g. a magnetic unit, that is surrounded by the housing unit, it is possible advantageously to expand the field of application of the housing unit in this way.

In an alternative embodiment of the invention, it is proposed that the at least two housing shell units should comprise in each case a front overlapping element and a rear overlapping element. In this context, a front overlapping element is understood in particular to be an overlapping element whose thickness is smaller than that of a central element of the housing shell unit, and which is so arranged as to be offset relative to a rear side of the central element and plane relative to a front side of the central element. A rear overlapping element here is understood in particular to be an overlapping element whose thickness is smaller than that of a central element of the housing shell unit, and which is so arranged as to be offset relative to a front side of the central element and plane relative to a rear side of the central element. The front overlapping element and the rear overlapping element are preferably arranged at opposite end regions and/or edge regions of the housing shell units. By virtue of this embodiment, it is structurally simple to arrange the housing shell units in a superimposed or overlapping manner relative to further housing shell units, and to avoid any undesired warping of the housing shell units and/or undesired enlargement of the housing unit.

It is further proposed that the overlapping elements should have a thickness which corresponds essentially to 50% of a thickness of a central element of the at least two housing shell units. It is thus possible, when there is an overlap and/or superimposition of the at least two housing shell units, to avoid any undesired warping of the individual housing shell units due to excessive material thickness in the regions of superimposition or overlap.

In a particularly advantageous development, the overlapping elements have in each case a length of at least 15% and at most 35% of the total length, along a direction of a total length of one of the at least two housing shell units. It is thereby possible to achieve a large adjustment region of the housing unit in respect of a dimension, in particular a length and/or a height and/or a width of a unit, in particular a magnetic unit, and a high degree of stability at the same time, wherein the high degree of stability of the housing shell units can be achieved by virtue of a large central region which has essentially twice the material thickness of the overlapping elements. Along the direction of the total length, the overlapping elements advantageously have a length of at least 20% and at most 35% of the total length, and preferably at least 25% and at most 30% of the total length.

In an advantageous development of the invention, it is proposed that at least one of the at least two housing shell units should feature a separating unit, which is formed on the at least one housing shell unit along a direction of a total length of one of the at least two housing shell units. In this way, with the aid of the at least one separating unit, the housing shell units can be truncated to a predetermined length and/or height, thereby advantageously increasing a variability and/or flexibility of the housing unit, e.g. in respect of a dimension of a unit that is surrounded by the housing unit, such as a magnetic unit in particular. It is advantageously possible to effect an adaptation of the housing shell units along a length and/or a width of the unit, in particular the magnetic unit, by means of the overlapping elements, and an adaptation of a height of the housing shell unit by means of the at least one separating unit. For example, the housing shell units can be designed for two different heights of units that are surrounded by the housing unit, in particular magnetic resonance devices, wherein the housing shell units can be used in their original form as a covering for a magnetic resonance device having a first height, and the housing shell units can be used in truncated form as a covering for a magnetic resonance device having a second height, which is smaller than the first height. A truncation of the housing shell units is preferably effected along the separating unit.

In a particularly advantageous development, the separating unit is formed by at least one elongated indentation and/or a multiplicity of indentations. In this context, the separating unit can be designed as predetermined break line, thereby allowing a particularly simple truncation of the housing shell units. Furthermore, the separating unit can form a type of guide groove along the indentations, e.g. for a saw tool, such that precise truncation of the housing shell units can be achieved. Alternatively, the separating unit can also take the form of a line, or similar, along which an operator can sever the housing shell units. The separating unit can be arranged on a front side of the housing shell units, such that an advantageous edge of cut can be achieved as a result of the indentations. Alternatively or additionally, the separating unit can also be arranged on a rear side of the housing shell units.

It is further proposed that at least one of the at least two housing shell units should be mounted on the support frame unit in such a way that it can be moved along at least one direction of a total length of one of the housing shell units for the purpose of assembly or disassembly. The housing shell units are preferably mounted on the support frame unit such that they can be moved towards each other, in particular along a direction of a total length of the housing shell units, such that the two housing shell units are so mounted on the support frame unit as to at least partially coincide. By virtue of this embodiment of the invention, it is advantageously possible to achieve a particularly flexible assembly, and to position the at least two housing shell units relative to each other with particular ease.

Moreover, it is proposed that at least one of the at least two housing shell units should feature at least one bearing element, allowing mobile mounting of the housing shell unit on the support frame unit. It is thereby possible advantageously to avoid and/or prevent in particular undesired friction damage and/or friction loss of the housing shell unit during assembly and/or disassembly of the housing shell unit. Assembly and/or disassembly of the housing shell units can also be developed in a user-friendly way. For example, the bearing element can be formed by a sliding bearing element and/or by other bearing elements that appear appropriate to a person skilled in the art. The housing shell units preferably feature at least two or more bearing elements in each case.

In a further embodiment of the invention, it is proposed that the support frame unit should feature at least one first support element and at least one second support element, wherein the at least one second support element is mounted on the at least one first support element in such a way that it can be moved in at least one direction for the purpose of assembly and/or disassembly. As a result, the support frame unit can advantageously be adapted to a length and/or height and/or a width of a unit that is surrounded by the housing unit, such as a magnetic unit in particular, and in this way the support frame unit can be used for covering differently embodied units, in particular magnetic units. The individual support elements can be developed from profiles made of aluminum, for example, and/or from other embodiments of the support elements that appear appropriate to a person skilled in the art. The direction preferably extends along a length of the at least one first support element.

It is further proposed that the at least one first support element and the at least one second support element should take the form of telescopic rods which can be pushed inside each other, whereby a particularly space-saving and compact support frame unit can be achieved.

It is further proposed that the at least one first support element should feature a holder in which a bearing element of the at least one second support element is movably mounted for the purpose of assembly or disassembly, thereby making it possible to provide a particularly stable and flexible support frame unit for a medical imaging device in particular.

Furthermore, the invention takes as its starting point a medical imaging device comprising a detector unit and a housing unit, which housing unit surrounds the detector unit and is developed in accordance with claim 1. The housing unit can thereby be adapted, in respect of a length and/or a width and/or a height, to a multiplicity of different medical imaging devices in a structurally simple manner, this being particularly advantageous.

BRIEF DESCRIPTION OF THE DRAWINGS

Further advantages, features and details of the invention are derived from the exemplary embodiments described below and with reference to the drawings, in which:

FIG. 5 shows a first housing unit for a first magnetic unit, FIG. 6 shows a second housing unit for a second magnetic unit.

DETAILED DESCRIPTION OF THE INVENTION

Figure 1:
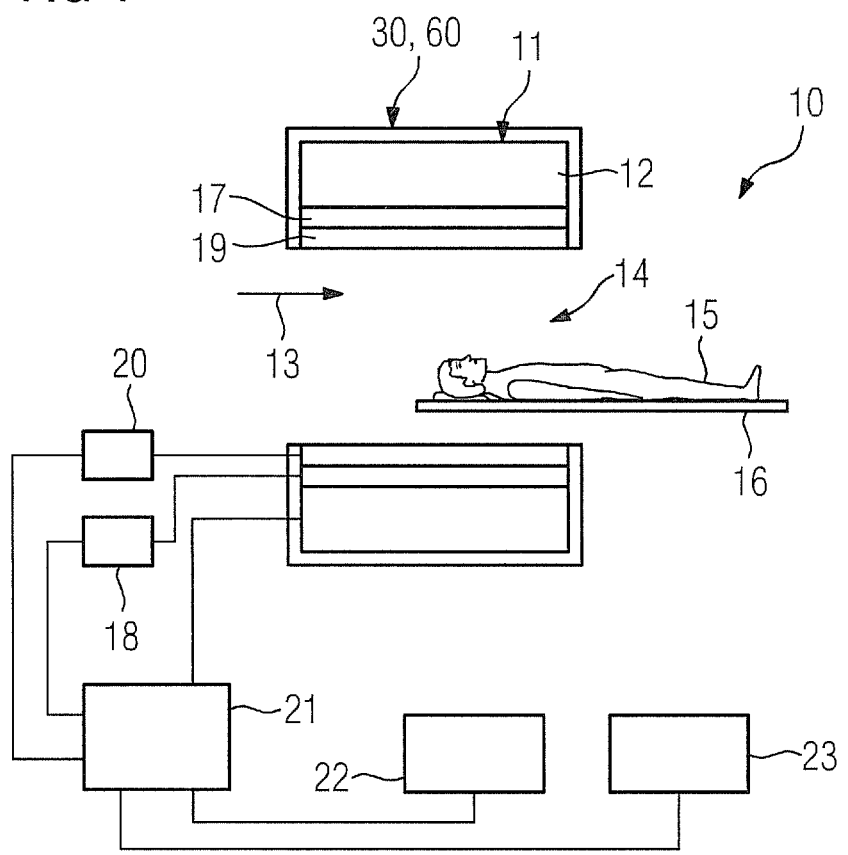
FIG. 1 shows a schematic illustration of a medical imaging device.

FIG. 1 schematically illustrates an example of a medical imaging device in the form of a magnetic resonance device 10. Alternatively, the medical imaging device can also take the form of a CT device or a PET device and/or further medical imaging devices that appear appropriate to a person skilled in the art.

The magnetic resonance device 10 comprises a detector unit in the form of a magnetic unit 11, which has a main magnet 12 for generating a strong and in particular constant main magnetic field 13. In addition, the magnetic resonance device 10 features a cylindrical holding region 14 for holding a patient 15, said holding region 14 being circumferentially surrounded by the magnetic unit 11. The patient 15 can be pushed into the holding region 14 by means of a patient couch 16 of the magnetic resonance device 10. For this purpose, the patient couch 16 is movably arranged within the magnetic resonance device 10. Furthermore, the magnetic resonance device 10 features a housing unit 30, 60 which surrounds the magnetic unit 11.

The magnetic unit 11 also features a gradient coil 17 for generating magnetic field gradients which are used for spatial encoding while imaging. The gradient coil 17 is controlled by means of a gradient control unit 18. Furthermore, the magnetic unit 11 features a high-frequency antenna 19 and a high-frequency antenna unit 20 for the purpose of stimulating a polarization which is established in the main magnetic field 13 that is generated by the main magnet 12. The high-frequency antenna 19 is controlled by the high-frequency antenna unit 20 and radiates high-frequency magnetic resonance sequences into an examination space that is essentially formed by the holding region 14. The magnetization is thereby deflected from its position of equilibrium. Furthermore, magnetic resonance signals are received by means of the high-frequency antenna 19 and the high-frequency antenna unit 20.

In order to control the main magnet 11, the gradient control unit 18 and the high-frequency antenna unit 20, the magnetic resonance device 10 has a control unit 21 in the form of an arithmetic-logic unit. The arithmetic-logic unit controls the magnetic resonance device 10 centrally, e.g. the execution of a predefined imaging gradient-echo sequence. Control information such as e.g. imaging parameters and reconstructed magnetic resonance images can be displayed on a display unit 22, e.g. at least one monitor, of the magnetic resonance device 10 for an operator. In addition, the magnetic resonance device 10 has an input unit 23, by means of which the information and/or parameters can be entered by an operator during a measurement procedure.

The magnetic resonance device 10 shown here can of course comprise further components which magnetic resonance devices 10 usually feature. Moreover, a general way in which a magnetic resonance device 10 functions is known to a person skilled in the art, and therefore a detailed description of the general components is not required.

The housing units 30, 60 presented below are designed for use with magnetic resonance devices 10. Therefore the housing units 30, 60 are designed to be compatible with magnetic resonance. In principle, it is of course also conceivable to use the housing units 30, 60 described below for other medical imaging devices, such as e.g. a CT device or PET device, etc. Moreover, it is of course also conceivable to use the housing units 30, 60 for other units and/or devices, whose design is different to that of a medical imaging device.

Figure 2:
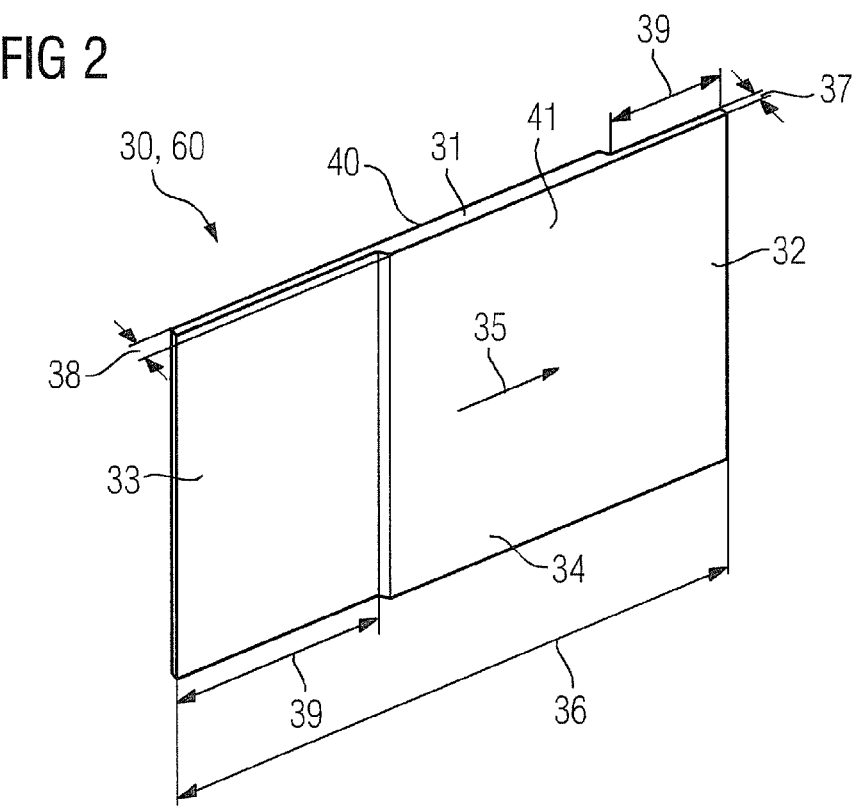
FIG. 2 shows a schematic illustration of a housing shell unit according to the invention.

By way of example, FIG. 2 then shows a housing shell unit 31 of the housing unit 30, 60 in greater detail. The housing shell unit 31 features two overlapping elements 32, 33 and a central element 34. The two overlapping elements 32, 33 are arranged along one direction 35 of a total length 36 of the housing shell unit 31 and at opposite end regions of the housing shell unit 31. Furthermore, the two overlapping elements 32, 33 have a thickness 37 which corresponds to essentially half of a thickness 38 of the central element 34. Along the direction 35 of the total length 36 of the housing shell unit 31, the overlapping elements 32, 33 have in each case a length 39 which corresponds to at least 10% of the total length 36 of the housing shell unit 31 and at most 35% of the total length 36 of the housing shell unit 31. However, the two overlapping elements 32, 33 advantageously have in each case a length 39 which is at least 20% of the total length 36 and at most 35% of the total length 36 of the housing shell unit 31, and preferably at least 25% of the total length 36 and at most 30% of the total length 36 of the housing shell unit 31.

In the present exemplary embodiment, the housing shell unit 31 has a total length 36 of approximately 1080 cm, wherein the central element 34 has a length of approximately 480 cm and the two overlapping elements 32, 33 have in each case a length 39 of approximately 300 cm.

A first of the two overlapping elements 32 is formed by a front overlapping element 32 and a second of the two overlapping elements 33 is formed by a rear overlapping element 33, this being apparent from FIG. 2 in particular. In this case, the front overlapping element 32 is so arranged as to be offset relative to a rear side and/or a rear wall 40 of the central element 34, wherein a step in a direction from the rear wall 40 to a front wall 41 of the central element 34 is arranged between the central element 34 and the front overlapping element 32. The front overlapping element 32 is so arranged as to be plane relative to the front wall 41 and/or a front side of the central element 34 of the housing shell unit 31. In this case, the rear overlapping element 33 so arranged as to be offset relative to the front side and/or front wall 41 of the central element 34, wherein a step in a direction from the front wall 41 to the rear wall 40 of the central element 34 is arranged between the central element 34 and the rear overlapping element 33. The rear overlapping element 33 is so arranged as to be plane relative to the rear wall 40 and/or the rear side of the central element 34 of the housing shell unit 31.

Figure 3:
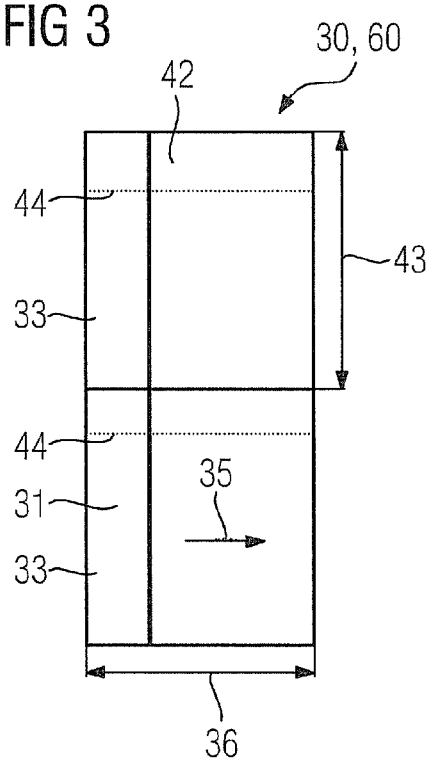
FIG. 3 shows two housing shell units with a separating unit which is indicated.
Figure 4:
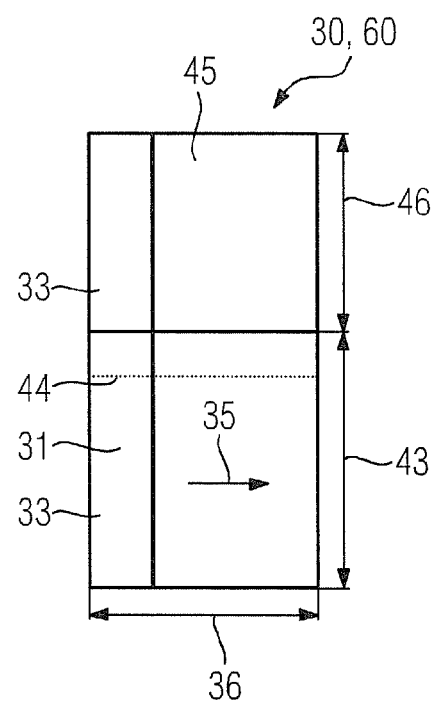
FIG. 4 shows two housing shell units with a truncation along the separating unit.

The housing shell unit 31 also features a separating unit 44, as indicated by a dotted line in the FIGS. 3 and 4 in particular. The separating unit 44 is arranged along the total length 36 of the housing shell unit 31 and on the front side thereof. In the present exemplary embodiment, the separating unit 44 is formed by an elongated indentation and/or a multiplicity of indentations, which are incorporated in the front wall 41 of the housing shell unit 31. In this case, the indentations are arranged consecutively along the direction 35 of the total length 36 of the housing shell unit 31, or the elongated indentation is arranged along the direction 35 of the total length 36 of the housing shell unit 31 on the front wall 41. Alternatively, the separating unit 44 can also be arranged on the rear wall 40 of the housing shell units 31.

By virtue of the indentations, it is particularly easy to truncate the housing shell unit 31 along these indentations because, for example, these indentations serve as a guide for a saw tool, in particular, or these indentations mark a predetermined breaking point of the housing shell unit 31, such that particularly simple severing of the housing shell unit 31 can be effected along the separating unit 44. Alternatively, the separating unit 44 can also consist merely of a line which is applied to the front wall 41 and/or to the rear wall 40 of the housing shell unit 31, and along which an intersection line for truncation of the housing shell unit 31 can be indicated for an operator.

Figure 7:
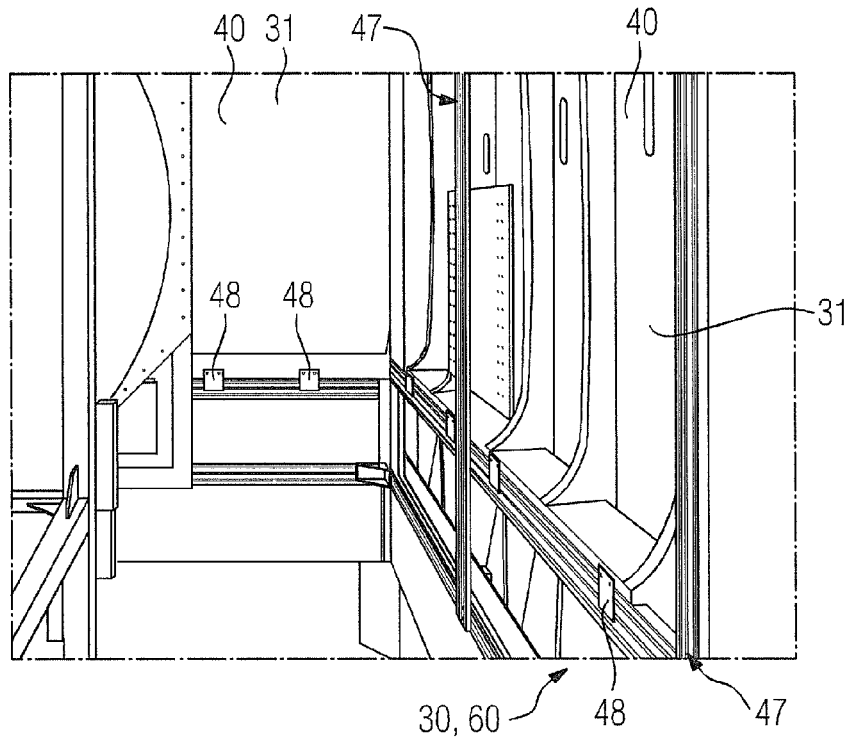
FIG. 7 shows a view of housing shell units which are mounted on a support frame construction.

Furthermore, the housing shell unit 31 features a plurality of bearing elements 48 as shown in FIG. 7. In the present exemplary embodiment, the housing shell unit 31 has two to four bearing elements 48. The bearing elements 48 are arranged on the rear wall 40 of the housing shell unit 31, wherein by means of the bearing elements 48 the housing shell unit 31 is so mounted on a support frame unit 47 of the housing unit 30, 60 that it can move along a direction 35 of a total length 36 of the housing unit 31. In the present exemplary embodiment, the bearing elements 48 are screwed onto the rear wall 40 of the housing shell unit 31 and are hung onto the support frame unit 47 of the housing unit 30 or engage in the support frame unit 47 during assembly of the housing shell unit 31. The housing shell unit 31 is thereby so mounted on the support frame unit 47 that it can be moved in an infinitely variable manner. Alternatively, it is possible to design the support frame unit 47 and/or the bearing elements 48 of the housing shell unit 31 in such a way that the housing shell unit 31 can only be mounted at defined positions, e.g. at predetermined locating positions, for the purpose of assembly and/or disassembly.

The housing shell unit 31 additionally has a curvature which is so embodied that the housing shell unit 31 can be used for different magnetic units 11 of different magnetic resonance devices 10 (FIG. 2).

Two housing shell units 31, 42, 45 are illustrated in each case in the FIGS. 3 and 4. The two housing shell units 31, 42, 45 are in each case designed in a similar manner to the housing shell unit 31 that is illustrated in FIG. 2, and are assembled together along a height 43.

The two housing shell units 31, 42 have an identical height 43 in FIG. 3. The two housing shell units 31, 45 have a different height 43, 46 in FIG. 4, however, wherein one of the two housing shell elements 45 is present here in a form that has been truncated along the separating unit 44.

Furthermore, it is also conceivable for both of the housing shell units 31, 45, as illustrated in FIG. 4 for a housing unit 30, 60, to be used in a form that is truncated along the separating unit 44.

FIGS. 5 and 6 show different housing units 30, 60 for different magnetic resonance devices 10. The individual housing units 30, 60 of the magnetic resonance devices 10 differ here in respect of a height and a length.

In FIG. 5, all of the housing shell units 31, 42 of the housing unit 30 are provided with an identical height 43 and an identical length, this being externally visible to an operator.

In FIG. 6, however, a housing unit 60 is illustrated in which the housing shell units 31 in a first row are provided with a first common height 43 and all of the housing shell units 45 in a second row are provided with a second common height 46, the second height 46 being smaller than the first height 43. In this context, all of the housing shell units 31, 45 of the second row were truncated to the second height 46 along the separating unit 44 prior to assembly.

Furthermore, the housing unit 30 features a support frame unit 47, which is illustrated in conjunction with the housing shell units 31 in greater detail in FIG. 7. In this case, the housing shell units 31 are mounted by means of the rear side or the bearing element 48 onto the support frame unit 47.

In order to assemble the individual housing shell units 31, for example, a first housing shell unit 31 can be assembled in a first position on the support frame unit 47. A second housing shell unit 31 can then be mounted on the support frame unit 47, and this housing shell unit 31, 42, 45 pushed into a second position on the support frame unit 47, for the purpose of positioning the second housing shell unit 31, until an optimal adaptation of the two housing shell units 31 to a dimension of the magnetic unit 11 is achieved, and an optimal overlap with the first housing shell unit 31 is also achieved. Only when an optimal adaptation to the dimension of the magnetic unit 11 and an optimal overlap between the first and the second housing shell unit 31 are achieved, is the second housing shell unit 31 fastened to the support frame unit 47 in this second position.

Figure 8:
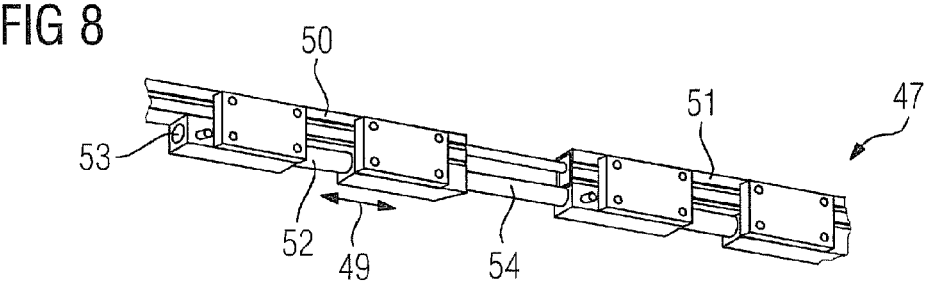
FIG. 8 shows a first embodiment of a support frame construction.

FIG. 8 shows a section of the support frame unit 47 in greater detail. The support frame unit features a plurality of support elements 50, 51, these being movably mounted relative to each other in order to allow adaptation of the support frame unit 47 to the magnetic unit 11, in particular to a dimension of the magnetic unit 11. In this context, a first support element 50 features a holding element 52 comprising a cylindrical holder 53, wherein the cylindrical holder 53 is constructed in the form of a tube. A further support element 51 of the support frame unit 57 features a cylindrical bearing element 54 which is mounted within the cylindrical holder 53 in such a way that it can be moved along a direction 49, such that the two support elements 50, 51 can be moved relative to each other by means of the bearing element 54 and the holder 53 for the purpose of adapting the support frame unit 47 to the magnetic unit 11.

Furthermore, the first support element 50 features a locking element, by means of which the cylindrical bearing element 54 can be locked within the cylindrical holder 53 in order to position the second support element 51 relative to the first support element 50. The locking element takes the form of a locking screw, for example, and/or other locking elements that appear appropriate to a person skilled in the art.

Figure 9:
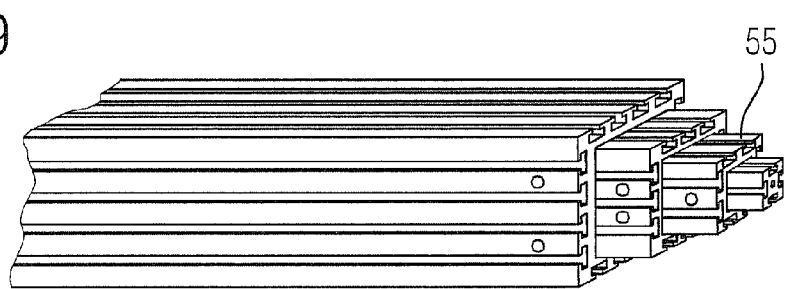
FIG. 9 shows a second embodiment of the support frame construction.

Alternatively, the support frame unit 47 can also take the form of telescopic rods 55 that can be pushed into each other as shown in FIG. 9.

Alternatively or additionally, the housing unit 30, 60 can also be designed such that the housing shell units 31, 42, 45 feature overlapping elements along two directions, these being perpendicular relative to each other, such that adaptation of the housing unit 30, 60 to a magnetic unit 11 is possible along at least two directions by means of the overlapping elements. The overlapping elements are conceivably made of a material that is at least partially flexible and/or elastic for this purpose.

The invention claimed is:

1. A housing unit for a medical imaging device, comprising:
    at least two housing shell units each comprising a first overlapping element, a second overlapping element and a central element extending from the first overlapping element to the second overlapping element, wherein a surface of at least one of the first and second overlapping along a length of each housing shell unit
    a support frame unit for mounting the at least two housing shell units,
    wherein the at least two housing shell units are configured to be overlapped in a region of the first and second overlapping elements of the at least two housing shell units when in an assembled position on the support frame unit.

2. The housing unit as claimed in claim 1, wherein the first and second overlapping elements are arranged at opposite end regions of each of the at least two housing shell units.

3. The housing unit as claimed in claim 2, wherein the first and second overlapping elements comprise a front overlapping element and a rear overlapping element.

4. The housing unit as claimed in claim 1, wherein a thickness of the overlapping elements is essentially 50% of a thickness of the central element.

5. The housing unit as claimed in claim 1, wherein a length of the overlapping elements is at least 10% and at most 35% of a total length of each of the at least two housing shell units.

6. The housing unit as claimed in claim 1, wherein a separating unit is formed on one of the at least two housing shell units along a direction of a total length of the one of the at least two housing shell units.

7. The housing unit as claimed in claim 6, wherein the separating unit is formed by an elongated indentation and/or a multiplicity of indentations.

8. The housing unit as claimed in claim 1, wherein one of the at least two housing shell units is movably mounted on the support frame unit and can be moved along a direction of a total length of the one of the at least two using shell units for assembly or disassembly.

9. The housing unit as claimed in claim 8, wherein the one of the at least two housing shell units is movably mounted on the support frame unit by a bearing element.

10. The housing unit as claimed in claim 1,
wherein the support frame unit comprises a first support element and a second support element, and
wherein the second support element is mounted on the first support element and can be moved along a direction for assembly and/or disassembly.

11. The housing unit as claimed in claim 10, wherein the first support element and the second support element are telescopic rods and can be pushed inside with each other.

12. The housing unit as claimed in claim 10,
wherein the first support element comprises a holder,
wherein the second support element comprises a bearing element, and
wherein the first support element is movably mounted on the bearing element of the second support element for assembly and/or disassembly.

13. The housing unit as claimed in claim 1, wherein the central element includes a front wall and a rear wall opposite to the front wall, and wherein the first overlapping element is arranged to be offset from the rear wall such that a step is between the central element and the first overlapping element, said step in a direction from the rear wall to the front wall.

14. The housing unit as claimed in claim 13, wherein the surface of the first overlapping element is plane relative to the front wall.

15. The housing unit as claimed in claim 13, wherein the second overlapping element is arranged to be offset from the front side such that a step is between the central element and the second overlapping element, said step in a direction from the front wall to the rear wall.

16. The housing unit as claimed in claim 15, wherein the surface of the second overlapping element is plane relative to the rear wall.

17. A housing unit for a medical imaging device, comprising:
at least two housing shell units each comprising an overlapping element and a central element, wherein a surface of the overlapping element is plane to a surface of the central element along a length of each housing shell unit; and
a support frame unit for mounting the at least two housing shell units,
wherein the at least two housing shell units are configured to be overlapped in a region of the overlapping element of the at least two housing shell units when in an assembled position on the support frame unit;
wherein a thickness of the overlapping element is essentially 50% of a thickness of the central element;
and wherein a length of the overlapping element is at least 10% and at most 35% of a total length of each of the at least two housing shell units.

18. The housing unit as claimed in claim 17, wherein the central element includes a front wall and a rear wall opposite to the front wall, and wherein the overlapping element is arranged to be offset from the rear wall such that a step is between the central element and the overlapping element, said step in a direction from the rear wall to the front wall.

19. The housing unit as claimed in claim 18, wherein the surface of the overlapping element is plane relative to the front wall.

* * * * *